United States Patent [19]

Haendle

[11] Patent Number: 4,481,651
[45] Date of Patent: Nov. 6, 1984

[54] X-RAY DIAGNOSTIC INSTALLATION FOR X-RAY TOMOGRAPHIC IMAGES

[75] Inventor: Joerg Haendle, Erlangen, Fed. Rep. of Germany

[73] Assignee: Siemens Aktiengesellschaft, Berlin & Munich, Fed. Rep. of Germany

[21] Appl. No.: 421,284

[22] Filed: Sep. 22, 1982

[30] Foreign Application Priority Data

Nov. 16, 1981 [DE] Fed. Rep. of Germany ....... 3145438

[51] Int. Cl.³ .............................................. G03B 41/16
[52] U.S. Cl. ........................................ 378/22; 378/99
[58] Field of Search .............................. 378/21, 22, 99

[56] References Cited
U.S. PATENT DOCUMENTS 4,149,082 4/1979 Haendle ................................ 378/22
4,349,740 9/1982 Grassman .............................. 378/22
4,442,534 4/1984 Haendle ................................ 378/22

Primary Examiner—Craig E. Church
Attorney, Agent, or Firm—Hill, Van Santen, Steadman & Simpson

[57] ABSTRACT

An exemplary embodiment includes a number of x-ray soures which are capable of being individually switched on in succession by means of a control generator, a patient support, an x-ray image intensifier which is surrounded by deflection coils which are connected with a deflection device, connected to the control generator, for the synchronous movement of the electron image in the x-ray image intensifier, a video camera which is aligned with the outlet fluorescent screen of the x-ray image intensifier, an image storage and a monitor, wherein the image storage is so designed that at least two groups of different individual images, superimposed, respectively, are capable of being stored. The control inputs of the image storage for the purpose of group-wise storage, are connected with the control generator. Associated with the image storage is a comparator which is so designed that it compares mutually corresponding image point data contained in the image storage and supplies only those particular image point data to the monitor which are in conformity.

5 Claims, 1 Drawing Figure

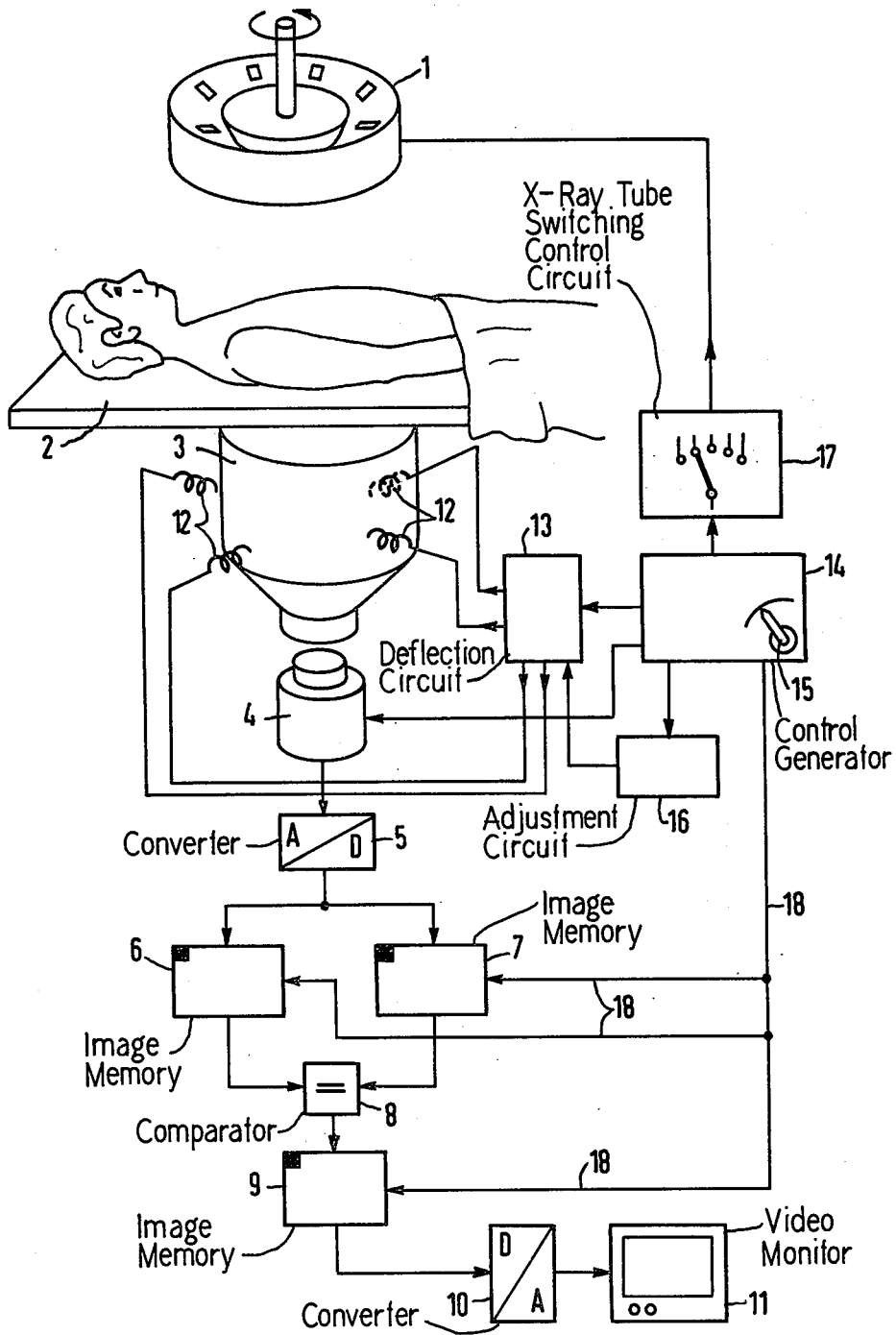

X-RAY DIAGNOSTIC INSTALLATION FOR X-RAY TOMOGRAPHIC IMAGES

BACKGROUND OF THE INVENTION

The invention relates to an x-ray diagnostic installation for x-ray tomographic images, comprising a number of x-ray sources which are capable of being individually sequentially switched-on by means of a control generator, comprising a patient support, comprising an x-ray image intensifier which is surrounded by deflecting coils which are connected with a deflection circuit, connected to the control generator, for the synchronous movement of the electron image in the x-ray image intensifier, comprising a video camera which is aligned with the outlet fluorescent screen of the x-ray image intensifier, comprising image storage means, and comprising a monitor. With this x-ray diagnostic installation one obtains x-ray tomographic images of a specific body layer in which interfering image superimpositions from other body layers are largely suppressed.

In U.S. Pat. No. 4,149,082 issued Apr. 10, 1979 such an x-ray diagnostic installation is described in which the synchronous movement of x-ray source and electron image in the x-ray image intensifier, necessary for tomographic images, proceeds by means of the activation of several linearly or circularly arranged x-ray tubes and simultaneous deflection of the electron image of the x-ray image intensifier. In dependence upon the adjusted deflecting amplitude of the electron image in the x-ray image intensifier and upon the geometric dimensions of the x-ray diagnostic installation, only one selected layer is represented in a sharply defined fashion, whereas all others are virtually suppressed due to lack of sharp definition. However, the body part disposed in the non-desired layer planes, in the case of strong x-ray absorption, can produce interfering blurring shadows.

SUMMARY OF THE INVENTION

The invention proceeds from the object of producing an x-ray diagnostic installation of the type initially cited wherein the interfering blurring shadows are virtually entirely eliminated.

In accordance with the invention, the object is achieved in that the image storage means are so designed that, in the latter, at least two groups of different individual images, superimposed, respectively, are capable of being stored, that the control inputs of the image storage means for the purpose of group-wise storage, are connected with the control generator, and that there is associated with the image storage means a comparator which is so designed that it compares mutually corresponding image point data contained in the image storage means and supplies only those particular image point data to the monitor which are in conformity. Through this inventive x-ray diagnostic installation the blurring shadows, which result due to offset individual images, are suppressed.

For the x-ray diagnostic installation a simple construction results if two image memories are connected in parallel to the output of the video camera. The blurring shadows can be particularly well obliterated if the control generator is so designed that, for the first group, it superimposes the individual images associated with the odd-numbered x-ray sources and, for the second group, the individual images associated with the even-numbered x-ray sources. The image memories can exhibit a simple construction if the control generator controls the scanning of the video camera in such a fashion that the individual images associated with the groups are successively superimposed on the target of the video camera. The x-ray diagnostic installation can also be operated in the fluoroscopy mode with a slightly reduced frame rate if the output of the comparator is connected with an additional image memory whose output signal is supplied to the monitor.

The invention shall be explained in greater detail in the following on the basis of an exemplary embodiment illustrated in the FIGURE on the accompanying drawing sheet; and other objects, features and advantages will be apparent from this detailed disclosure and from the appended claims.

BRIEF DESCRIPTION OF THE DRAWINGS

The single FIGURE is a diagrammatic view showing an x-ray diagnostic installtion according to the invention.

DETAILED DESCRIPTION

In the FIGURE an x-ray diagnostic installation according to the invention with an x-ray tube 1 is illustrated which exhibits a circular ring-shaped arrangement of grid-controlled cathodes which are arranged about a rotary anode. An x-ray tube of this type is described in the German patent application No. P 31 13 368.1. Instead of this one specific x-ray tube 1, however, also several individual x-ray tubes can be employed which can be arranged in a circular ring fashion or in a linear fashion and can be switched on synchronously with the deflection of the image of an x-ray image intensifier 3.

The high voltage generator for the x-ray tube 1 is not illustrated. The x-ray tube 1 generates x-ray beams which penetrate a patient lying on a patient support 2 from various directions and cast radiation images on the inlet fluorescent screen of the x-ray image intensifier 3. The output signal of the x-ray image intensifier 3 is picked up by a video camera 4 which is connected to an analog-to-digital converter (A/D-converter) 5. The digital output signal of the A/D-converter 5 is supplied to two parallel-connected image memories 6 and 7. The outputs of the two image memories 6 and 7 are connected with the inputs of a comparator 8 whose output signal is stored in an additional image memory 9. The output signals of the image memory 9 are converted in a digital-to-analog converter (D/A-converter) 10 to analog video signals and are displayed on a monitor 11.

The deflection of the electron image in the x-ray image intensifier 3—necessary for tomographic technique—corresponding to the direction of the respectively switched-on x-ray beam, is magnetically achieved by means of two pairs of deflection coils 12. The activation of the deflection coils 12 proceeds by means of a deflection circuit 13 which is synchronized by a control generator 14. The extent of displacement of the electron image is selected with an adjustment means 15 which can be designed in the form of a potentiometer, which is secured to the control generator 14. The extent of the displacement determines the height of the body layer under consideration. The displacement of the electron image is effected by means of an electron image positioning adjustment circuit 16 which is connected with the control generator 14 and the deflection circuit 13. The control generator 14 effects, synchronously with the image displacement in the x-ray image intensifier 3, via a control circuit 17, the step-by-step switching-on of the grids of the x-ray tube 1. For this purpose, a stepping switch can be provided in the control circuit 17, as illustrated.

The control generator 14 is connected via clock pulse and control lines such as 18 with the video camera 4 and the image memories 6, 7, and 9. Via these lines the control generator 14 controls the scanning of the target in the video camera 4 and the storage operations in the image memories 6, 7, and 9. For the generation of the control pulses, the controlgenerator 14 can include an oscillator, frequency divider, flip-flop circuits, and logic circuit elements such as indicated in the fifth Figure of U.S. Pat. No. 4,149,082.

Influenced by the control generator 14, the control circuit 17 switches on the grids of the x-ray tube 1 subdivided in step-by-step fashion into groups. The first group can, for example, be formed from the odd-numbered x-ray sources, and the second group can be formed from the even-numbered x-ray sources (where the ring of x-ray sources of x-ray tube 1 are assigned sequential numbers). However, a subdivision can also take place in which the first group is formed from the first half of the x-ray sources, and the second group is formed fromthe second half (each group occupying a 180° segment of the illustrated x-ray tube 1). First, the x-ray sources of the first group are successively switched on by the control generator 14. In the video camera 4, whose scanning beam is blocked during the exposure of the individual images associated with the first group, these individual images are superimposed on the target. After exposure has taken place, the target is scanned and the video signals are read into the image memory 6. Subsequently, with a blocked scanning beam of the video camera 4, the second group of x-ray sources is switched-on whose individual images, superimposed on the target of the video camera 4, after completed exposure, are scanned jointly and stored in the image memory 7. The image point data contained in the image memories 6 and 7 are compared in point-by-point fashion in the comparator 8. If both image point data agree, then this information is transmitted into the image memory 9. If, by contrast, the compared image point data exhibit different values, the latter are not stored. An image thereby results in the image memory 9 which consists only of the image point data which exhibit equal values in both groups. However, this is the case only with those image point data which pertain to the desired layer selected by the adjustment means 15. The image point data originating from the points lying outside the desired layer are not stored in the image memory 9 and are thus not imaged on the monitor.

The comparator 8 can, for example, be constructed from several 4-bit-comparator circuits of the type 7485 (with separate A=B output). The output signal from the comparator can be supplied to an AND-circuit, to the other input of which is connected a control signal for effecting the storing of the image point data, contained in the image memories 6 or 7, into the image memory 9.

However, alternatively, the memory clock pulse can be directly supplied by the control generator 14 to the image memory 9. Then the output signal of the comparator 8 controls AND-circuits which are series connected with the outputs of the image memories 6 or 7.

Instead of the superimposition of the individual images on the target and the control of the scanning of the video camera tube connected therewith, the video camera 4 can operate in continuous operation if the image memories 6 and 7 are so designed that they render possible a summation of the image point data sequentially supplied thereto.

If, by contrast, the superimposition, as described, takes place on the target of the video camera 4, then either the image memory 7 or the image memory 9 can be dispensed with. If the image memory 7 is dispensed with, then, as described, the first group of individual images is read into the image memory 6. If the second group of superimposed individual images is scanned by the video camera 4, then this group is immediately supplied to the comparator 8 and compared in image-point fashion with the group stored in the image memory 6. If, by contrast, both image memories 6 and 7 are present, then the output image as selected by the comparator 8 can be directly represented on the monitor 11.

It will be apparent that many modifications and variations may be effected without departing from the scope of the novel teachings and concepts of the present invention.

I claim as my invention:

1. An x-ray diagnostic installation for x-ray tomographic images, comprising a control generator, a number of x-ray sources (1) controlled by the control generator so as to be switched on individually in succession by means of the control generator (14), a patient support (2), an x-ray image intensifier (3) having deflection coils (12), deflection means (13) connected to the deflection coils and controlled by the control generator (14) for effecting synchronous movement of the electron image in the x-ray image intensifier (3), a video camera (4) coupled with the outlet fluorescent screen of the x-ray image intensifier, image storage means (6, 7), and a monitor (11), characterized in that the image storage means (6, 7) are so designed that at least one of two groups of different individual images, superimposed, respectively, is capable of being stored therein, that the control inputs of the image storage means (6, 7), for the purpose of group-wise storage, are connected with the control generator (14), and that comparator means (8) is associated with the image storage means (6, 7) for comparing mutually corresponding image point data comprising that contained in the image storage means (6, 7) and supplying only those particular image point data to the monitor which are in conformity.

2. An x-ray diagnostic installation according to claim 1, characterized in that said image storage means comprises two image memories (6, 7) both connected to the output of the video camera (4) for receiving respective groups of superimposed images for subsequent point by point comparison.

3. An x-ray diagnostic installation according to claim 1, characterized in that the control generator (14) is so designed that, for the first group, it superimposes the individual images associated with the odd-numbered x-ray sources and, for the second group, it superimposes the individual images associated with the even-numbered x-ray sources.

4. An x-ray diagnostic installation according to claim 1, characterized in that the control generator (14) controls the scanning of the video camera (4) in such a fashion that the individual images associated with at least one of the groups are successively superimposed on the target of the video camera (4), and then scanned as a superimposed image for storage.

5. An x-ray diagnostic installation according to claim 1 with an additional image memory (9), characterized in that the output of the comparator (8) is connected with the additional image memory (9) for selecting a resultant image for storage in said additional image memory based on the image point data which are in conformity.

* * * * *